(12) United States Patent
Bicknell et al.

(10) Patent No.: US 9,545,484 B2
(45) Date of Patent: Jan. 17, 2017

(54) NEEDLE SHIELD ARRANGEMENT

(75) Inventors: Stephen Bicknell, Warwickshire (GB); Jeremy Marshall, Oxford (GB)

(73) Assignee: OWEN MUMFORD LIMITED, Oxford (GB)

( * ) Notice: Subject to any disclaimer, the term of this patent is extended or adjusted under 35 U.S.C. 154(b) by 63 days.

(21) Appl. No.: 13/823,432

(22) PCT Filed: Oct. 11, 2011

(86) PCT No.: PCT/GB2011/051960
§ 371 (c)(1),
(2), (4) Date: Apr. 25, 2013

(87) PCT Pub. No.: WO2012/049493
PCT Pub. Date: Apr. 19, 2012

(65) Prior Publication Data
US 2013/0204197 A1 Aug. 8, 2013

Related U.S. Application Data

(60) Provisional application No. 61/392,205, filed on Oct. 12, 2010.

(30) Foreign Application Priority Data

Oct. 12, 2010 (GB) .................................. 1017180.9

(51) Int. Cl.
*A61M 5/32* (2006.01)
*A61M 5/20* (2006.01)
(Continued)

(52) U.S. Cl.
CPC ......... *A61M 5/3202* (2013.01); *A61M 5/3204* (2013.01); *A61M 5/20* (2013.01);
(Continued)

(58) Field of Classification Search
CPC ................. A61M 2005/206; A61M 2005/312; A61M 5/20; A61M 5/3202; A61M 5/3204; A61M 2005/3117; A61M 2005/3118
(Continued)

(56) References Cited

U.S. PATENT DOCUMENTS 6,053,892 A 4/2000 Meyer
6,102,893 A 8/2000 Aneas
(Continued)

FOREIGN PATENT DOCUMENTS

GB 927626 A 5/1963
GB 2424836 A 10/2006
(Continued)

OTHER PUBLICATIONS

British Search Report, dated Dec. 15, 2010, from corresponding British Search Report.
(Continued)

*Primary Examiner* — Rebecca E Eisenberg
(74) *Attorney, Agent, or Firm* — Young & Thompson

(57) ABSTRACT

A needle shield arrangement for a syringe (10), having a generally cylindrical body with a needle (16) at its forward end, includes a shield portion (20) adapted for shielding the needle (16); a syringe engaging portion (22) for engagement with the syringe body, and a frangible connecting portion (24) connecting the shield portion and the syringe engagement portion.

20 Claims, 2 Drawing Sheets

(51) Int. Cl.
*A61M 5/31* (2006.01)
*A61M 5/34* (2006.01)

(52) U.S. Cl.
CPC ....... *A61M 5/343* (2013.01); *A61M 2005/206* (2013.01); *A61M 2005/312* (2013.01)

(58) Field of Classification Search
USPC .................. 604/110–111, 197–198, 218, 272
See application file for complete search history.

(56) References Cited

U.S. PATENT DOCUMENTS

| | | |
|---|---|---|
| 2002/0002354 A1 | 1/2002 | Vetter et al. |
| 2003/0093037 A1 | 5/2003 | Parker et al. |
| 2004/0186440 A1* | 9/2004 | Jansen et al. ................. 604/198 |
| 2007/0017533 A1 | 1/2007 | Wyrick |
| 2009/0234297 A1* | 9/2009 | Jennings ....................... 604/195 |
| 2013/0150801 A1* | 6/2013 | Ekman et al. ................. 604/198 |

FOREIGN PATENT DOCUMENTS

| | | |
|---|---|---|
| GB | 2425062 A | 10/2006 |
| GB | 2465389 A | 5/2010 |
| JP | H11-505739 | 5/1999 |
| JP | 2001-506508 | 5/2001 |
| JP | 2003-516794 | 5/2003 |
| WO | 01-43619 | 6/2001 |
| WO | 03/095002 A1 | 11/2003 |
| WO | 2007-008257 | 1/2007 |

OTHER PUBLICATIONS

International Search Report, dated Dec. 8, 2011, from corresponding PCT application.
JP Office Action, dated Sep. 1, 2015; Application No. 2013-533286.

* cited by examiner

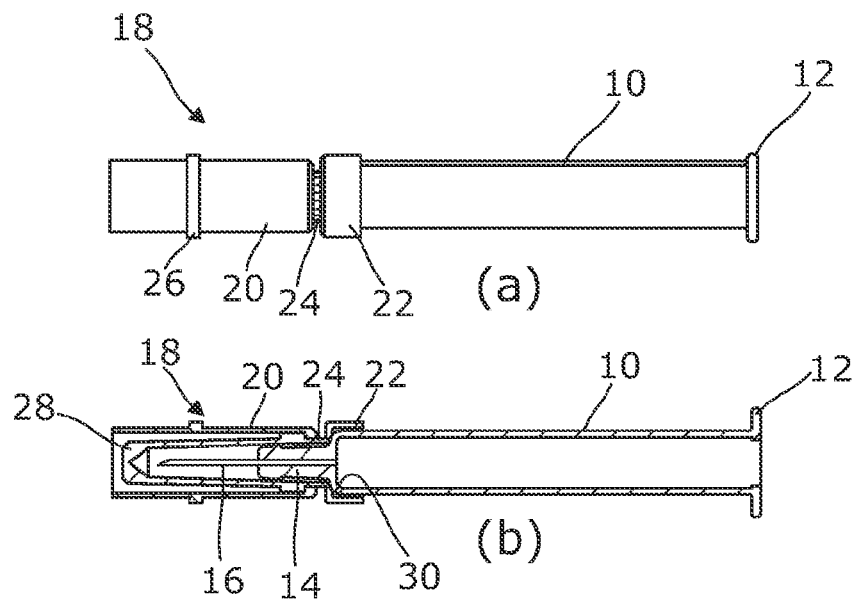
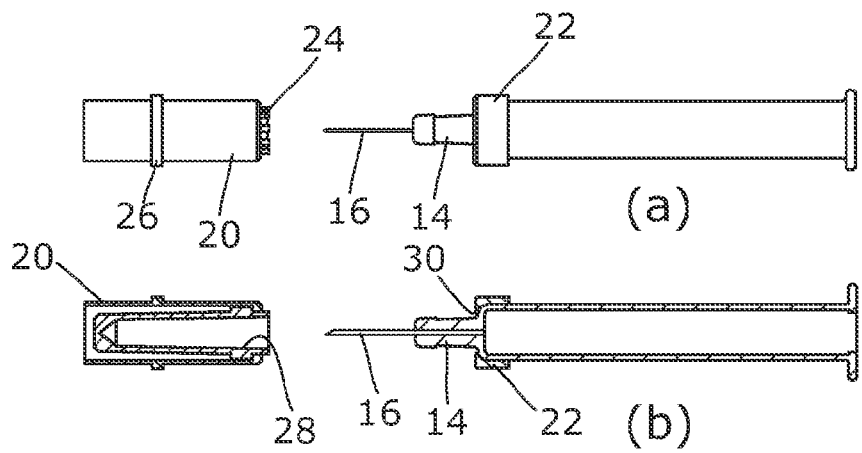
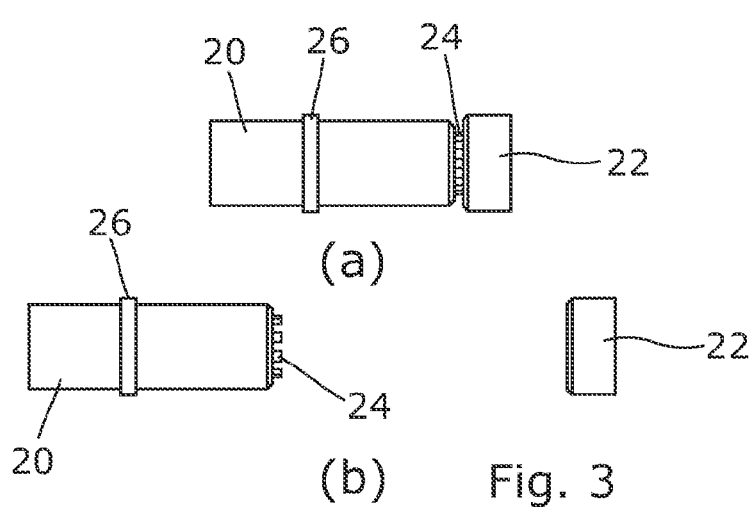
Fig. 1
Fig. 2
Fig. 3

NEEDLE SHIELD ARRANGEMENT

BACKGROUND OF THE INVENTION

Field of the Invention

This invention relates to needle shield arrangements and to injection apparatus incorporating such arrangements. It is known to provide a syringe shield to cover the needle of a syringe prior to injection to maintain sterility of the needle, to avoid evaporation of a medicament contained within the syringe, to prevent needle stick injuries and also to protect the needle during manufacture and assembly of injection devices. In a known form of rigid needle shield arrangement, a soft rubber inner boot fits over a ribbed spigot at the forward end of the syringe body and the boot is contained by an outer rigid cylindrical portion. In such arrangements, the needle shield is a slip fit over the spigot and there is no connection between the shield and the syringe body.

Description of the Related Art

In addition, in autoinjector devices where a syringe or cartridge is initially driven forwardly in a penetration phase to insert the needle into the flesh, there is usually some arresting action on the syringe when it is in its forwardmost position. Often, that arresting force is passed to the syringe flanges either directly or via a cylindrical syringe carrier or the like. Because the flanges extend at right angles to the barrel of the syringe, the angle acts as a stress magnifier and there is a risk that the flange breaks off so that the syringe shoots forwardly beyond its required position. Also, we have found that, because of an accumulation of tolerances the tolerance of the distance between the needle tip and the flange surface is relatively large. Since the movement of the syringe, the penetration depth of the needle and other injection characteristics are affected by the accumulated tolerance between the reference surface on the syringe and the needle front tip, it is important to reduce this. The accumulated tolerance would be reduced if the forwarding facing load-bearing surface on the syringe were forwardly of the flange. It is also preferred to pass the restraint load into the cylindrical wall of the syringe in axial alignment with the wall, not only to reduce offset loads but also to allow the diameter of any arresting surface or spring to be relatively high so as not to obstruct the area in front of the syringe which may house an arresting spring, a needle shield remover and so on.

GB2424836 discloses an injection device in which a tamper-evident needle shield is connected to a needle hub by a frangible connection. The needle hub is a separate item fitted onto the tip of the syringe rather than the body thereof. There is no suggestion of reacting any restraint load via the portion of the needle hub that remains after removal of the needle shield.

GB2425062 discloses in FIGS. 6 and 7 an injection device in which a needle cap connected to a needle sub-assembly by a frangible connection. The needle sub-assembly is fitted onto the tip of the syringe. There is no disclosure of any needle shield arrangement in which a shield portion is frangibly connected to a portion that engages the main body of the syringe, nor of an arrangement in which the syringe engaging portion receives all or part of the arresting load as the syringe is arrested at the end of its extension movement.

U.S. Pat. No. 6,053,892, WO03/095002 and GB927626 each disclose a hypodermic syringe head with a tamper-evident seal. Again, this has a hub that fits onto the tip of the syringe.

SUMMARY OF THE INVENTION

In order to address at least some of these issues, we have designed a needle shield assembly where the assembly is removably secured to the main body of the syringe thereby providing stability for the needle shield and also preferably providing a reaction surface through which loads may be transmitted to or sustained by the syringe body, rather than through the syringe flange.

Accordingly, in one aspect, this invention provides a needle shield arrangement for a syringe, the syringe having a generally cylindrical body with a needle at its forward end, the arrangement comprising:

a shield portion adapted for shielding said needle;

a syringe engaging portion for engagement with said syringe body, and a frangible connecting portion connecting said shield portion and said syringe engagement portion.

In the above arrangement the shield arrangement is at least partly supported relative to the syringe by the syringe engaging portion. Prior to use, the shield portion may be detached by breaking the connecting portion, leaving the syringe engaging portion in place. The syringe engaging portion can be used to react or transfer loads on the syringe for example when a dose is expressed from the syringe or, in some instances, where the syringe is mounted in a housing for movement between retracted and extended positions.

Although the syringe engaging portion could engage or be secured to the syringe body at any point along its length, it is preferred for the syringe engaging portion to engage a forward end portion of the cylindrical main body of the syringe, to the rear of a reduced diameter tip. In this manner, loads may be transferred to and from the syringe body through the body itself rather than through the rearward flange of the syringe or the reduced diameter tip. Also, the restraint force can be aligned with the cylindrical wall.

Where the syringe is of typical form with a forward facing circumferential shoulder at its forward end to provide the reduced diameter front tip, the syringe engagement portion is conveniently complementarily shaped to engage said shoulder. For example it may form a syringe engaging cup with angular contact around the forward facing shoulder of the syringe which provides a structurally strong region to transmit load. There may be circular, or interrupted circular contact between the tip and the shoulder.

Although it would be possible for the syringe engaging portion to be bonded to or to grip the associated surface of the syringe, it is preferred for the syringe engaging portion to be a sliding fit with the front end of the syringe, with the grip between the needle shield and the needle tip or spigot initially holding the syringe engaging portion against forward movement.

Conveniently, the shield portion and the syringe engaging portion are each solids of revolution about a longitudinal axis, and the frangible connecting portion comprises a concentric plurality of frangible tabs connecting the two.

The invention also extends to a needle shield arrangement separate from a syringe and also in combination therewith.

The invention further extends to an injection apparatus comprising:

an elongate housing;

a syringe mounted in said housing for longitudinal movement and having a generally cylindrical body with a needle at its forward end;

a needle shield arrangement comprising;

a shield portion adapted to shield said needle;

a syringe engaging portion for engagement with said syringe body; and a frangible connecting portion connecting said shield portion and said syringe engaging portion;

the apparatus including a stop element for arresting forward movement of said syringe beyond a forward position, wherein at least part of the arresting load is transmitted to said syringe via said syringe engaging portion.

The stop element may be e.g. a stop surface or other suitable stop, for example a spring that acts as a stop when fully compressed.

Whilst the invention has been described above it extends to any inventive combination of the features set out herein or in the attached drawings.

BRIEF DESCRIPTION OF THE DRAWING FIGURES

The invention may be performed in various ways, and, by way of example only, a specific embodiment will now described, reference being made to the accompanying drawings, in which:

FIGS. 1(a) and (b) are side and longitudinal section views respectively through a syringe fitted with a needle shield assembly of this invention;

FIGS. 2(a) and (b) are side and longitudinal section views similar to FIG. 1 but showing the needle shield portion after detachment from the syringe, leaving the syringe engaging portion in place;

FIGS. 3(a) and (b) are side views showing the needle shield assembly before and after detachment of the needle shield portion;

DETAILED DESCRIPTION OF THE INVENTION

Figure 4:
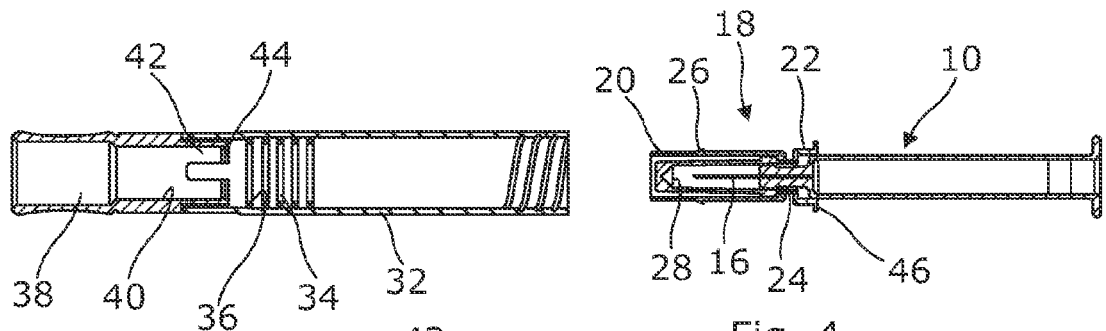
FIG. 4 shows the assembly of FIG. 1 prior to installation into an injector housing.

Referring initially to FIGS. 1(a) and (b), there is shown a syringe of conventional form comprising a generally cylindrical barrel 10 having a flange 12 at its rear end and a tip or spigot 14 of reduced diameter from which projects the needle 16 at its forward end. Fitted on the forward end of the syringe body is a needle shield assembly 18 comprising a needle shield portion 20 connected to a syringe engaging collar 22 by means of frangible tabs 24. The needle shield portion, syringe engaging collar and tabs are a one piece monolithic plastics moulding. The needle shielding portion 20 is of cylindrical form and provided with an integral circumferential rib 26 partway down the body. Retained inside the needle shielding portion 20 is a soft rubber boot 28 which is a slideable friction fit at its rear end over the tip or spigot 14. The syringe engagement collar 22 is of cup shaped form and engages the forward facing shoulder 30 of the barrel 10. As shown in FIG. 2, the syringe shielding portion, with soft rubber boot 28 inside it can be detached from the syringe to expose the syringe needle 16, leaving the collar 22 in engagement with the syringe. The needle shielding portion 20 can be detached by pulling or twisting, or a claw, lever or the like may be inserted in the gap between the collar 22 and the shield portion 20 to prise the two apart.

Referring now to FIGS. 4 to 7, as shown in the schematic representation of the assembly and operation of one particular embodiment. In this arrangement, the syringe 10 with needle shield assembly 18 attached is inserted into the generally cylindrical forward housing 32 of an autoinjector. In the rear part (shown substantially at 11) there is provided a drive mechanism for applying a forward drive force to urge the syringe forwardly to a limit position and thereafter to expel a dose through the needle. Suitable such mechanisms are well known to those skilled in the art and so will not be described in detail here. A compression spring 34 is located in a forward end of the housing 32 with the forward end of the spring 34 abutting an internal shoulder 36 in the housing.

Figure 5:
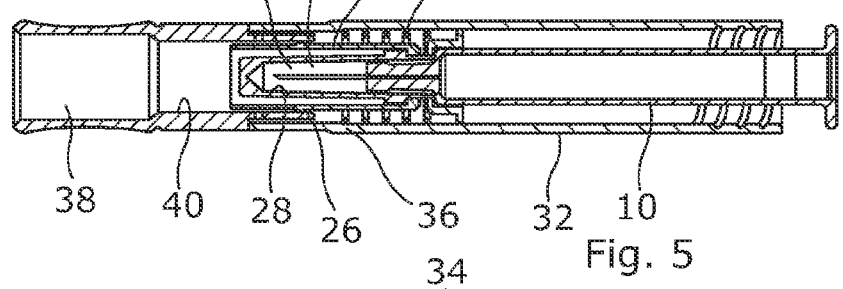
FIG. 5 is a view similar to FIG. 4 but after installation.
Figure 6:
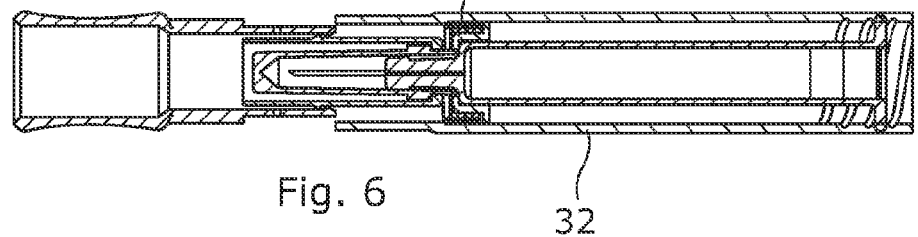
FIGS. 6 and 7 are successive views showing removal of the needle shield portion as a forward cap is removed from the injector housing.
Figure 7:
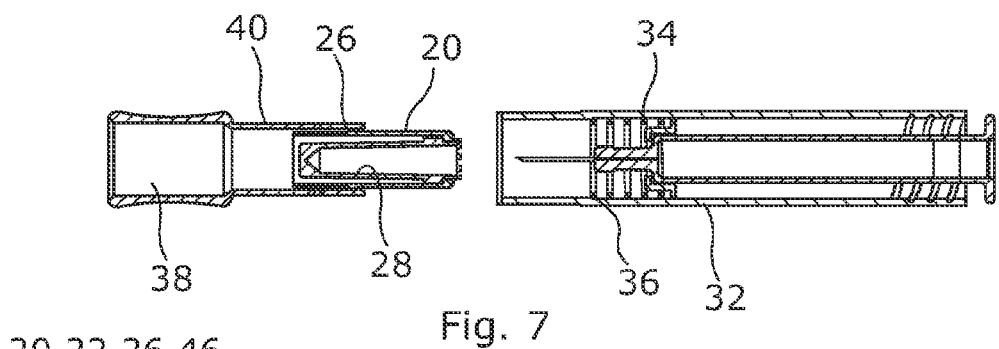

A shield remover cap 38 is slideably received in the forward end of the housing 32 and has a rearwardly extending cylindrical portion 40 slotted to provide resiliently deformable fingers 42 with inwardly directed barbs 44. During assembly, the syringe and needle shield assembly are inserted longitudinally into the housing and pushed forwardly so that the barbed fingers 42 snap past the cylindrical rib 26 on the needle shield portion. An outer flange 46 on the syringe engaging collar 22 abuts the rear end of the spring 34, as shown in FIG. 5. In order to prepare the syringe for injection, the cap 38 is pulled forwardly so that the barbed fingers 42 engage the rib 26, and the needle shield portion is pulled off the syringe, breaking the tabs 24. As this happens the syringe is pulled forwardly, with the spring 34 compressing and bottoming out.

In use, the injection device is offered up to the injection site and the drive mechanism fired. During an initial phase of the autoinjection movement, the syringe is moved bodily forward relative to the housing 32 until it is arrested by the spring 34 bottoming out. It will be noted that the arresting force is therefore applied to the front end of the syringe into the cylindrical wall thereof, rather than the rear end. Thereafter the dose is expressed and the injection complete.

Figure 8:
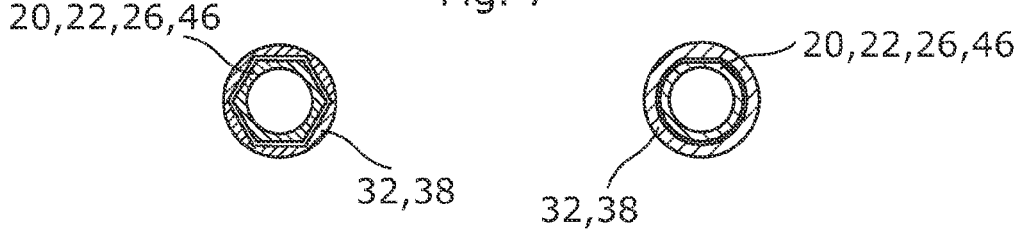
FIG. 8 shows various interfaces for use between the cap and the exterior of the needle shield portion, and between the interior of the housing and the syringe engaging collar.

In a modified arrangement, one or more of the outer flange 46, the collar 22, the needle shielding portion 20 and the circumferential rib 26 may have an outer periphery of non-circular form adapted to engage a complementary shaped cooperating portion on the interior of the syringe housing 32, or the interior of the cap 38 respectively so that twisting motion may be applied to the needle shield 18 and the collar 22 by twisting the cap 38 relative to the syringe housing, thereby to break the tabs 24 by torsion. Examples of suitable inner and outer interfaces between the components are shown in FIG. 8. Thus, one possible interface is hexagonal, and another possible interface is circular with a 10 flat.

The invention claimed is:

1. A needle shield arrangement for mounting on a syringe, the syringe having a generally cylindrical body, a needle at a forward end of the syringe, and a flange at a rear end of the syringe; and an autoinjector housing in which the syringe and the needle shield arrangement are mounted, the needle shield arrangement comprising:

a shield portion adapted for shielding said needle;

a syringe engaging portion for engagement with said syringe body; and a frangible connecting portion connecting said shield portion and said syringe engagement portion, wherein the syringe engaging portion of the needle shield arrangement includes a forward facing reaction surface through which loads may be transmitted to or sustained by the syringe body, such that in use, when the syringe and the needle shield portion are urged forward in the housing of the autoinjector, syringe movement is arrested by a stop surface in the housing, and at least part of an arresting load is transmitted to the generally cylindrical body of said syringe via the reaction surface on the syringe engaging portion of the needle shield assembly.

2. The needle shield arrangement according to claim 1, wherein said syringe engaging portion is adapted to engage a forward end portion of the syringe.

3. The needle shield arrangement according to claim 2, wherein said syringe body is formed with a forward facing circumferential shoulder at a forward end of the syringe body, and said syringe engagement portion is complimentarily shaped to engage said shoulder.

4. The needle shield arrangement according to claim 2, wherein said syringe engaging portion is slideably adapted to receive a forward end of the syringe body.

5. The needle shield arrangement according to claim 1, wherein said shield portion and said syringe engaging portion are each solids of revolution about a longitudinal axis, and said frangible connecting portion comprises a concentric plurality of frangible tabs connecting said shield portion and said syringe engaging portion.

6. The needle shield arrangement according to claim 1, wherein an outer peripheral portion of at least one of the shield portion and the syringe engaging portion is non-circular, thereby in use allowing non-rotational engagement with an outer component.

7. The method of assembly of an injection device which comprises applying a needle shield arrangement according to claim 1 to the forward end of a syringe and thereafter introducing the syringe and needle shield arrangement forwardly into a rear end of a generally tubular housing portion having a cap removably attached to a front end thereof to cause the shield portion to be captured by said cap, whereby removal of said cap removes said shield portion leaving said syringe engaging portion adjacent said syringe body.

8. The needle shield arrangement according to claim 1, wherein said forward facing reaction surface of the syringe engaging portion is beveled.

9. The needle shield arrangement according to claim 1, wherein said frangible connecting portion comprises frangible tabs.

10. The needle shield arrangement according to claim 1, wherein said shield portion is integral with a circumferential rib.

11. An injection apparatus comprising:
an elongate housing;
a syringe mounted in said elongate housing for longitudinal movement and having a generally cylindrical body with a needle at a forward end of the syringe, the syringe being mounted in said elongate housing for longitudinal movement; and
a needle shield arrangement comprising:
a shield portion adapted to shield said needle,
a syringe engaging portion for engagement with said syringe body, and a frangible connecting portion connecting said shield portion and said syringe engaging portion;

wherein, in use, the needle shield arrangement is fitted on the syringe; and the syringe and needle shield arrangement are mounted in the elongate housing for longitudinal movement;
the elongate housing includes a stop surface for arresting forward movement of said syringe beyond a forward position;
the syringe engaging portion includes a forward facing reaction surface; and
wherein, in use, when the syringe is urged forward in the elongate housing, syringe movement is arrested by the stop surface and at least part of an arresting load is transmitted to the generally cylindrical body of said syringe via the reaction surface on said syringe engaging portion of the needle shield arrangement.

12. The injection apparatus according to claim 11, which includes a frangible connecting portion connecting said shield portion and said syringe engaging portion.

13. The injection apparatus according to claim 12, wherein a region of the syringe engaging portion is in non-rotational engagement with said elongate housing, and thereby prevented from rotation with respect thereto.

14. The injection apparatus according to claim 12, including a cap fitted into a forward end of the elongate housing and adapted to engage and remove the shield portion upon withdrawal of the cap from the forward end of the elongate housing, and a region of the shield portion is in non-rotational engagement with said cap, whereby rotary motion applied to said cap is transmitted to said shield portion.

15. The injection apparatus according to claim 11 wherein said syringe body is formed with a flange at its rearward end and said syringe engaging portion engages said syringe body at a location spaced forwardly of said flange.

16. The injection apparatus according to claim 15, including a cap fitted into the forward end of the elongate housing and adapted to engage and remove the shield portion upon withdrawal of the cap from a forward end of the elongate housing, and a region of the shield portion is in non-rotational engagement with said cap, whereby rotary motion applied to said cap is transmitted to said shield portion.

17. The injection apparatus according to claim 11, including a cap fitted into the forward end of the elongate housing and adapted to engage and remove the shield portion upon withdrawal of the cap from the forward end of the elongate housing, and a region of the shield portion is in non-rotational engagement with said cap, whereby rotary motion applied to said cap is transmitted to said shield portion.

18. The injection apparatus according to claim 11, wherein said forward facing reaction surface of the syringe engaging portion is beveled.

19. The injection apparatus according to claim 11, wherein said frangible connecting portion comprises frangible tabs.

20. The injection apparatus according to claim 11, wherein said shield portion is integral with a circumferential rib.

* * * * *